(12) United States Patent
Verschoor et al.

(10) Patent No.: US 9,506,913 B2
(45) Date of Patent: Nov. 29, 2016

(54) METHOD OF DETECTING SURROGATE MARKERS IN A SERUM SAMPLE

(75) Inventors: Jan Adrianus Verschoor, Pretoria (ZA); Mervyn Beukes, Pretoria (ZA)

(73) Assignee: University of Pretoria, Pretoria (ZA)

( * ) Notice: Subject to any disclaimer, the term of this patent is extended or adjusted under 35 U.S.C. 154(b) by 0 days.

(21) Appl. No.: 13/810,275

(22) PCT Filed: Jul. 12, 2011

(86) PCT No.: PCT/IB2011/053108
§ 371 (c)(1),
(2), (4) Date: Jan. 15, 2013

(87) PCT Pub. No.: WO2012/007903
PCT Pub. Date: Jan. 19, 2012

(65) Prior Publication Data
US 2013/0137598 A1 May 30, 2013

(30) Foreign Application Priority Data

Jul. 15, 2010 (ZA) .................................... 10/05040

(51) Int. Cl.
*G01N 33/53* (2006.01)
*G01N 33/569* (2006.01)
*C07K 16/44* (2006.01)
*G01N 33/558* (2006.01)

(52) U.S. Cl.
CPC .............. *G01N 33/53* (2013.01); *C07K 16/44* (2013.01); *G01N 33/558* (2013.01); *G01N 33/5695* (2013.01); *C07K 2317/23* (2013.01); *C07K 2317/33* (2013.01); *C07K 2317/622* (2013.01)

(58) Field of Classification Search
None
See application file for complete search history.

(56) References Cited

U.S. PATENT DOCUMENTS

| 3,789,116 | A | * | 1/1974 | Kay | ...................... G01N 33/582 436/547 |
| 5,721,109 | A | * | 2/1998 | Yano et al. | ................... 435/7.32 |
| 2003/0143652 | A1 | * | 7/2003 | Simonson | .................... 435/7.32 |

FOREIGN PATENT DOCUMENTS

| WO | WO 95/28642 A1 | 10/1995 | |
| WO | WO 9528642 A1 * | 10/1995 | ........... G01N 33/569 |
| WO | WO 2005/116654 A1 | 12/2005 | |

OTHER PUBLICATIONS

O'Farrell (2009) "Evolution in Lateral Flow-Based Immunoassay Systems" In: Lateral Flow Immunoassay, pp. 1-33, eds RC Wong and HY Tse, Humana Press, NY, New York.*
Benadie Y et al: "Cholesteroid nature of free mycolic acids from M. tuberculosis.", Chemistry and Physics ofLipids, Limerick, IR, vol. 152, No. 2, Apr. 1, 2008 (Apr. 1, 2008 ), pp. 95-103.
Y. Lemmer et al: "Detection of antimycolic acid antibodies by liposomal biosensors." Methods in Enzymology, vol. 464, 2009, pp. 79-104, Elsevier Academic Press Inc.
Thanyani et al: "A novel application of affinity biosensor technology to detect antibodies to mycolic acid in tuberculosis patients.", Journal of Immunological Methods, vol. 332, No. 1-2, Jan. 11, 2008, pp. 61-72.
World Health Organization, Geneva CH 2008: "Diagnostics Evaluation Series No. 2: Laboratory-based evaluation of 19 commercially available rapid diagnostic tests for tuberculosis." Jan. 1, 2008, pp. 1-70; retrieved from the internet: URL: http://apps.who.int/tdr/publications/tdr-research-publications/diagnostics-evaluation-2/pdf/diagnostic-evaluation-2.pdf.
International Search Report prepared by the European Patent Office on Jan. 23, 2012, for International Application No. PCT/IB2011/053108.

* cited by examiner

*Primary Examiner* — Tracy Vivlemore
*Assistant Examiner* — Karen S Weiler
(74) *Attorney, Agent, or Firm* — Sheridan Ross P.C.

(57) ABSTRACT

The present invention relates to a method of detecting an active tuberculosis infection in a serum sample from an individual. More specifically, the disclosed method uses a single chain variable fragment from a monoclonal immunoglobulin specific for mycolic acids of mycobacterial origin to detect surrogate markers, the presence of which indicate the individual has an active tuberculosis infection. Markers useful for practicing the disclosed method can be serum mycolic acid antigen, serum anti-mycolic acid antibodies or both. In a preferred embodiment, the method is practiced using a lateral flow assay format.

10 Claims, 1 Drawing Sheet

METHOD OF DETECTING SURROGATE MARKERS IN A SERUM SAMPLE

CROSS REFERENCE TO RELATED APPLICATIONS

Figure 1:
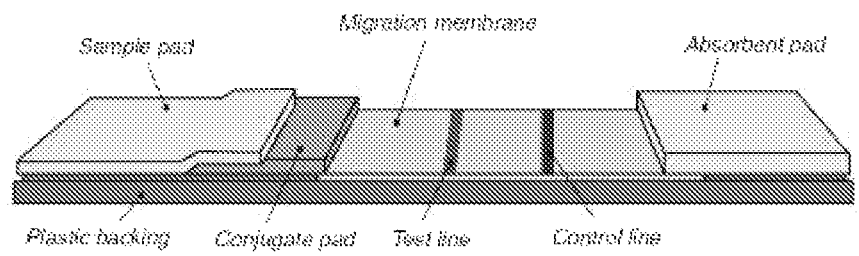

This application is a national stage application under 35 U.S.C. 371 and claims the benefit of PCT Application No. PCT/IB2011/053108 having an international filing date of 12 Jul. 2011, which designated the United States, which PCT application claimed the benefit of South African Application No. 2010/05040 filed Jul. 15, 2010, the disclosure of both the above-identified applications are incorporated herein by reference.

REFERENCE TO SEQUENCE LISTING

This application contains a Sequence Listing submitted as an electronic text file named "P49728ZP00_Sequence_listing_ST25.TXT", having a size in bytes of 4 KB, and created on Dec. 13, 2012. The information contained in this electronic file is hereby incorporated by reference in its entirety pursuant to 37 CFR §1.52(e)(5).

THIS INVENTION relates to a method for detecting active tuberculosis. It relates, in particular, but not exclusively to a method which can be used at point of care clinics.

More specifically, the invention relates to a serodiagnostic method for tuberculosis or TB based on the prevalence in mammalian subjects of either antibodies to lipid antigens, or lipid antigens derived from *Mycobacterium tuberculosis*. For a disease such as tuberculosis, there has to date been no acceptable serodiagnostic assay, despite the fact that much progress has been reported in studies of antibodies to various antigens of *M. tuberculosis* in the serum of patients with TB (Pan et al., 1999; Julian et al., 2002; Schleicher et al., 2002; Lopez-Marin et al., 2003; Pottunarthy et al., 2000, Steingart et al., 2007).

South Africa currently has the highest incidence of TB per 100 000 people in the world. In 2007 alone 112 000 people died of TB in South Africa, of which 94 000 were co-infected with HIV (WHO, 2009). Two thirds of these deaths could be prevented if they were diagnosed in time. One of the biggest challenges facing clinicians is the time it takes to accurately diagnose TB. Currently, using the conventional methods, it takes on average 4 weeks to diagnose TB which leads to a delay in treatment of the disease. If a fast diagnosis is available patients would receive anti-TB therapy immediately and become non-infective within a few days. With the current methods of diagnosis, patients with persistent symptoms have to remain in quarantine for several weeks while awaiting the results. During this time, they can infect the medical staff, their next of kin or anyone with whom they share a closed area, such as in public transport. The rise of MDR and XDR TB poses a threat of spreading among hospital staff and the communities an almost incurable disease that can be fatal within two months. The need for a fast, reliable diagnostic tool for TB is therefore high, especially in high HIV incidence populations (Wood et al., 2007).

Immunodiagnostic assays detecting pathogen related antibodies in patient sera with active TB disease is an attractive alternative for rapid diagnosis. An array of mycobacterial cell wall components have been considered as antigens for surrogate marker antibodies for TB in the past (Fujiwara et al., 1999; Lyashcenko et al., 1998, Nabeshima et al., 2005). Antigenic activity of mycolic acids and the glycolipid derivatives such as the lipid extractable trehalose mono- or dimycolates, TMM or TDM respectively (cord factors) have been reviewed recently (Sekanka et al., 2007). Of all the antigens prevalent in the cell wall of the mycobacteria that may be considered for use in TB serodiagnosis, mycolic acids provide a special opportunity due to their abundance, variability among different species of *Mycobacterium* and the unique way that they communicate their presence to the immune response of the host (Sekanka et al., 2007; Shui et al., 2007; Yuan et al., 1997). The ability of mycolic acids to elicit CD4-, CD8-double negative T cells by means of their presentation on CD1b proteins of dendritic cells (Beckman et al., 1994) may well be the reason that the antibody titers to mycolic acids in AIDS patients with even very low CD4 T cell counts are maintained, relative to other patients that are not infected with HIV, or have normal CD4 T cell counts (Schleicher et al., 2002). Pan et al. have shown that the most antigenic part of the cord factor antigen was the mycolic acid (Pan et al., 1999).

The use of mycolic acid antigens to detect antibodies as surrogate markers for TB diagnosis was shown to be feasible in an ELISA assay (Pan et al., 1999; Schleicher et al., 2002), albeit of limited accuracy. One complication was the cross-reactivity of human serum antibodies between mycolic acids and cholesterol that gave rise to a high antibody binding signal with human TB negative sera against mycolic acid. This was most likely due to a shared structural feature between cholesterol and a folded form of mycolic acid, as both cholesterol and mycolic acids could be liganded by Amphotericin B, a cholesterol binding drug (Benadie et al., 2008). The cross-reactivity could be due to a mixture of monospecific anti-cholesterol and anti-MA antibodies in the sera, or due to a true cross-reactivity where a particular antibody specificity could recognize both mycolic acid and cholesterol. It is known that all humans have anti-cholesterol antibodies in their blood circulation (Swartz et al., 1988), which may explain the high antibody activity to mycolic acids in TB negative patients. A biosensor approach showed improved accuracy to a level that may warrant consideration for commercialization, when using free mycolic acids in liposomes as antigens in a competitive binding assay (Lemmer et al., 2009; Thanyani et al., 2008). This test, subsequently dubbed the MARTI-test (for Mycolic acids Antibody Real-Time Inhibition), can diagnose TB within four hours of sampling by analyzing the serum sample for the presence of anti-mycolic acid antibodies as immune surrogate markers for active TB that is accurate even in HIV infected patients. The use of the inhibition of binding of antibodies in a real-time immunoassay seemed to largely solve the problem of cross-reactivity between mycolic acids and cholesterol.

Mycolic acids (MA) are high molecular weight, α-alkyl, β-hydroxyl fatty acids and are characteristic components of the cell envelope of mycobacteria and some other bacterial genera. In the mycobacterial cell envelope, MA are present as free lipid esters, such as trehalose dimycolate (TDM) or cord factor and trehalose monomycolate (TMM), but for the most part, they are esterified to the terminal penta-arabinofuranosyl units of arabinogalactan, a peptidoglycan-linked polysaccharide (Brennan and Nikaido, 1995). The presence of such long-chain fatty acids is largely responsible for the high hydrophobicity and very low permeability of the mycobacterial cell envelope (Lee et al., 1996). The number of carbon atoms that make up the MA varies from $C_{20}$ to $C_{36}$ in the genus *Corynebacterium* to $C_{60}$ to $C_{90}$ in the genus *Mycobacterium*. MA of the *Nocardia* and *Rhodococcus* species have lengths ranging from $C_{36}$ to $C_{66}$ (Butler et al., 1991). Mycobacterial MA compose about 40-60% of the dry weight of the cell wall of the bacteria (Brennan and Nikaido, 1995; Lee et al., 1996). Because of the uniqueness of the structures of mycolic acids to the pathogenic *Mycobacterium tuberculosis*, they provide ideal antigens for serodiagnosis of tuberculosis.

Mycolic acids comprise a large number of various structures within and among *Mycobacterium* species and in a few other genera. In *M. tuberculosis*, they consist mainly of alpha-, keto- and methoxy-MA subclasses, each of varying chain lengths and particular stereochemical structure around the functional groups in the main (mero-) chain (Dobson et al. 1985). Whether all, a few, or one of these MAs are detected as antigens by TB patient antibodies is not clear at this stage and is a focus of current research. Pan et al. (1999) indicated that the oxygenated natural MAs, i.e. keto- and methoxy-MA, are more antigenic than the non-oxygenated alpha MA, but the observations are not yet conclusive as the MAs were tested as methyl-esters, rather than as free mycolic acids. A more sensitive and specific diagnostic assay could possibly be developed by making use of specific synthetic stereo controlled mycolic acid subclasses instead of using natural mixtures of MA that could differ between batches. Because different MA subclasses dominate in certain stages of the growth of mycobacteria or stage of disease, it could also be that a specific synthetic MA antigen could provide more reliable data, reveal information on the stage of the disease and be better able to distinguish between TB positive and TB negative patient sera. Achievement of the stereocontrolled chemical synthesis of various subclasses of mycolic acids representative of those that appear in the cell wall of *M. tb* was reported since 2005 (Al Dulayymi 2005, 2006 and 2007, Toschi 2006, Koza 2007).

DESCRIPTION OF THE STATE OF THE ART

Patent Application No. PCT/GB95/00856 (Verschoor and Bye, 1995) describes the incorporation of mycolic acid in an immunogenic conjugate which elicited specific antibody production in mice. Optimization of a procedure for extraction and purification of mycolic acids of mycobacteria was disclosed in Patent Application No. PCT/GB96/00416 (Verschoor, 1996 and Goodrum et al., 2001). The immunological properties of the mycolic acids were tested in TB infected animals and in vitro cultures of human cells to explore the potential for broader application of the patented principles and products of tuberculosis. This work has been compiled in subsequent Patent Application No. PCT/GB98/00681 (Verschoor et al., 1998) and published (Korf et al., 2005). In the USA, four divisional patent applications based on this patent application were filed of which divisional application PAl29709/US relating to the use of anti-mycolic acid antibodies in human subjects as surrogate markers for TB infection was conditionally allowed in the USA in 2002. The claims were substantiated by the presentation of experimental data in 2005, when the prevalence of anti-mycolic acid antibodies in serum samples of human TB patients could be demonstrated with adequate accuracy using wave-guide biosensor technology (Verschoor et al. 2005, Thanyani et al. 2008). The test was subsquently named the MARTI test for TB serodiagnosis (Lemmer et al. 2009) and shown to work in a surface plasmon resonance biosensor as well. It was also shown to work by means of electro-impedance spectroscopy (Mathebula et al. 2009, Ozoemena et al. 2010).

In its configuration as an evanescent field or electro-impedance biosensor, the MARTI-test remains laboratory bound, i.e. suitable only for use in a TB reference laboratory. This is due to the requirement of highly skilled laboratory staff, sophisticated equipment and an air-conditioned, dust free environment. In order for the process to work in the field, i.e. at the point of care clinics, it would be desirable if the principles of the MARTI-test could be reconfigured in a simple dip-stick format as a lateral flow immunoassay.

Lateral flow immunoassays were first described in the 1960s and have since become popularly known as 'dip-stick tests'. The first commercial application was a home pregnancy test launched in 1988. Since then, the technology has been applied in a range of tests for clinical, veterinary, agricultural, food industry and environmental applications. Dip-stick strip tests are versatile and are available for a range of analytes from low molecular weight molecules and proteins to whole viruses and bacteria. Variations of the technology have been developed into a number of commercial products, but they all operate according to the same basic principle (adapted from Food Safety Info, www.foodsafetywatch.com, viewed in March 2010).

In a dip-stick immunoassay, lateral flow of sample and reagents occur along a single axis on a test strip format, starting from a sample deposition pad, followed by a conjugate pad and proceeding over a reaction membrane towards a wick that serves as a waste reservoir (as shown in FIG. 1). The sample pad is an absorbent pad onto which the test sample is applied. Antibodies or antigen binding fragments of antibodies directed to the target analytes are put in the conjugate or reagent pad. They are conjugated to reporter molecules such as colloidal gold or fluorophores. The reaction membrane is typically composed of a hydrophobic nitrocellulose or cellulose acetate membrane onto which anti-target analyte antibodies are immobilised in a line across the membrane as a capture zone or test line. A control zone may also be present that contains antibodies specific for the conjugate antibodies. In competitive immunoassay dip-sticks, the capture zone on the membrane may contain immobilised antigens. The wick or waste reservoir is a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones.

There are two main types of lateral flow immunoassay, namely double antibody sandwich and competitive assays. In double antibody sandwich assay the sample migrates from the sample pad through the conjugate pad where any target analyte present will bind to the conjugate. The sample then continues to migrate across the membrane until it reaches the capture zone where the target/conjugate complex binds to the immobilised antibodies producing a visible line on the membrane. The sample then migrates further along the strip until it reaches the control zone, where excess conjugate binds to produce a second visible line on the membrane. This control line indicates that the sample has migrated across the membrane as intended. Two clear lines on the membrane is a positive result. A single line in the control zone is a negative result. Double antibody sandwich assays are most suitable for larger analytes, such as bacterial pathogens and viruses, with multiple antigenic sites. Competitive assays are primarily used for testing small molecules and differ from the double antibody sandwich format in that the conjugate pad contains labelled antibodies that are already bound to a target analyte, or to an analogue of it. If the target analyte is also present in the sample it will therefore not bind with the conjugate and will remain unlabelled. As the sample migrates along the membrane and reaches the capture zone an excess of unlabelled analyte will bind to the immobilised antibodies and block or outcompete the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present in the sample, a weak line may be produced in the capture zone, indicating an inconclusive result. Competitive assays are most suitable for testing for small molecules unable to bind to more than one antibody simultaneously. There are a number of variations on lateral flow technology. The capture zone on the membrane may contain immobilised antigens rather than antibodies. It is also possible to apply multiple capture zones to create a multiplex test.

Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

While most lateral flow immunoassays are only capable of providing a qualitative result, it is possible to obtain some degree of quantification by measuring the amount of conjugate bound to the capture zone. This can be done using a dedicated reader to measure the intensity of the coloured test line. More sophisticated techniques, such as fluorescent dye labelled conjugates, have also been developed to improve the quantitative potential of lateral flow assays.

The present invention provides a lateral flow immunoassay specifically for diagnosis of tuberculosis from a few drops of blood from the patient. The test is specifically aimed to give a first indication of TB at a point of care setting such as a rural clinic. It will be of particular benefit to communities where HIV abounds, as the test should not be affected by co-infection of the patient with HIV. At the completion of the test, the user may read the test results by eye, or have it measured in a specifically designed scanner that gives a quantitative readout. If both the test and control lines are coloured, the test is negative for TB. If only the control line is coloured, the test is positive for active TB. The test is referred to as MALIA (Mycolic acids Antibodies Lateral flow Immuno Assay).

SUMMARY OF THE INVENTION

The invention provides a method of detecting surrogate markers for active tuberculosis in a serum sample, the surrogate markers being selected from serum mycolic acid antigen arising from tuberculous mycobacterial infection, serum anti-mycolic acid antibodies arising from tuberculous mycobacterial infection or both, the method including the steps of combining the serum sample with a labelled monoclonal immunoglobulin antibody or fragment thereof to mycolic acids to produce a combined serum sample, the antibody or fragment thereof not substantially cross-reacting with cholesterol and the label being selected so that binding of the labelled antibody to immobilized mycolic acid antigen of mycobacterial origin produces a detectable signal;

combining a blank sample with the labelled monoclonal immunoglobulin antibody or fragment thereof to mycolic acid to produce a combined blank sample; and then exposing both the combined serum sample and the combined blank sample to immobilised mycolic acid antigen of mycobacterial origin or a synthetic analogue or analogues thereof so that the labelled immunoglobulin antibodies or fragments thereof in each sample bind to the immobilised antigen to produce detectable signals, the signal produced by the combined blank sample being stronger than that produced by the combined serum sample because of inhibition of binding of the labelled antibody in the exposed serum sample arising from prior binding of the labelled monoclonal antibody with the mycolic acid antigen in the serum sample or by competitive binding of serum anti-mycolic acid antibodies in the serum sample to the immobilised mycolic acid antigen or both.

The method may include combining the serum sample and the blank sample in a conjugate pad of a lateral flow immunoassay device and exposing the combined serum sample and the combined blank sample to immobilized mycolic acids in a capture zone of the lateral flow immunoassay device. The sample may be of human or animal origin.

The method may then include exposing the remainders of the combined serum sample and the combined blank sample to immobilized anti-immunoglobulin antibodies in a control zone of the lateral flow immunoassay device.

The analyte serum antibodies may thus be antibodies against *Mycobacterium tuberculosis*, or antibodies against part thereof. The antibodies may be of the types that demonstrate cross-reactivity towards sterols such as cholesterol. The antibodies may be low affinity antibodies The serum sample and the blank sample may thus be exposed to the labelled antibody or fragment thereof in a conjugate pad, after which they migrate to a capture zone where the exposed serum sample and the exposed blank sample are exposed to the immobilised antigen. From there, the remainders of the serum sample and the blank sample migrate to a control zone where they are exposed to the immobilized anti-immunoglobulin antibodies that can bind unbound labelled antibody or fragment thereof onto the control zone. The capture and control zones thus make up two zones of the lateral flow immunoassay device.

The labelled monoclonal immunoglobulin antibody or fragment thereof may be labelled with colloidal gold or with a suitable fluorophore or chromophore such as latex or fluorescent beads so that the signal is a colour signal. For example a significantly faded colour in the capture zone for the serum sample in comparison to that of the blank sample will thus indicate a positive result, under the condition that the control zone exposed to either serum sample or blank sample both become equally coloured. When gold coated colloidal particles mix, they produce colour of low-density, due to natural repellent forces that keep them at a distance from one another. When gold-labelled antibody binds to immobilised antigen, the repellent forces between the gold particles are overcome. The gold particles then merge their magnetic fields with one another and produce an intense colour in the visible spectrum.

According to a second aspect the invention provides a method of detecting surrogate markers for active tuberculosis in a serum sample by lateral flow immunoassay using a lateral flow assay device, the device including a sample pad, a conjugate pad, a capture zone, at least two lanes and optionally a control zone, the surrogate markers being selected from serum mycolic acid antigen arising from tuberculous mycobacterial infection, serum anti-mycolic acid antibodies arising from tuberculous mycobacterial infection or both, the method including the steps of immobilizing isolated mycolic acid antigen of mycobacterial origin or a synthetic analogue or analogues thereof in the capture zone, optionally immobilizing anti-immunoglobulin antibodies that recognize the monoclonal antibody or fragment thereof in the control zone, providing a labeled monoclonal immunoglobulin antibody or fragment thereof to mycolic acids in the conjugate pad, the antibody not substantially cross-reacting with cholesterol and the label being selected so that binding of the labelled antibody or fragment thereof to the mycolic acid antigen of mycobacterial origin produces a detectable signal, applying the serum sample from a person or animal suspected of having tuberculosis to the sample pad of a first lane of the lateral flow device;

applying a blank sample comprising a buffer solution to the sample pad of a second lane of the lateral flow device;

allowing the serum sample and the blank sample to be transferred to the conjugate pad so that the serum mycolic acid antigen, the serum anti-mycolic acid antibodies or both in the serum sample and the buffer solution in the blank sample mix in the conjugate pad with the labelled monoclonal immunoglobulin antibody;

allowing the serum sample with the labelled monoclonal immunoglobulin antibody in the first lane and the blank sample with the labelled monoclonal antibody in the second lane to be transferred to the capture zone to allow binding of the labelled monoclonal antibody and the serum anti-mycolic acid antibody in the first lane and the labelled monoclonal antibody in the second lane to the immobilised mycolic acid in the capture zone and detecting inhibition of binding of the labelled antibody to the mycolic acid antigen in the capture zone by a reduction in the strength of the signal produced by the serum sample, compared to that produced by the blank sample because of inhibition of binding of the labelled monoclonal antibody arising from prior binding with the serum mycolic acid antigen in the serum or by competitive binding of serum anti-mycolic acid antibodies in the serum sample to the immobilised mycolic acid antigen, or both; and optionally allowing remainders of the combined serum sample and the combined blank sample to be transferred to the control zone to allow binding of the remaining labelled monoclonal antibody to the immobilised anti-immunoglobulin antibodies in the control zone in order to confirm that the flow of serum sample and blank sample to the absorbent pad happened in both lanes by the appearance of binding signals on the control zones in both lanes According to a third aspect, the invention provides a lateral flow immunoassay device for detecting surrogate markers for active tuberculosis in a serum sample, the surrogate markers being selected from serum anti-mycolic acid antigen arising from tuberculous mycobacterial infection, serum mycolic acid antibodies arising from tuberculous mycobacterial infection or both, the device including a sample pad, a conjugate pad, a capture zone and, optionally, a control zone, the conjugate pad containing a labelled monoclonal immunoglobulin antibody to mycolic acids which is not substantially cross-reactive with cholesterol, the label being selected so that binding of the labelled antibody to mycolic acid antigen of mycobacterial origin produces a detectable signal, the capture zone comprising immobilised isolated mycolic acid antigen of mycobacterial origin or a synthetic analogue or analogue thereof and the optional control zone comprising immobilised anti-immunoglobulin antibodies that can bind to the labelled monoclonal antibodies.

The labelled monoclonal immunoglobulin antibody or fragment thereof to mycolic acids may be a colloidal gold labelled monoclonal immunoglobulin antibody or fragment thereof to mycolic acids. The mycobacterial infection may be of the type which causes diseases selected from pulmonary tuberculosis and other forms of tuberculosis. The serum mycolic acid antigen may be a from mycobacteria selected from virulent and pathogenic tuberculous mycobacteria. In particular, the mycolic acid antigen may be derived from *Mycobacterium tuberculosis*.

The monoclonal immunoglobulin antibody may be a recombinant single chain, variable fragment of monoclonal immunoglobulin (scFv) directed to mycolic acid. The scFv antibody fragment may be selected from a vertebrate immunoglobulin gene library. In particular, the scFv antibody fragment may be selected from a chicken immunoglobulin gene library.

The scFv antibody fragment may be substituted by a larger fragment of the immunoglobulin or the full monoclonal immunoglobulin or by a number of fragments linked to a carrier protein. The serum mycolic acid antibodies may include types that demonstrate cross-reactivity towards sterols. The scFv antibody fragment may have the amino acid sequence of Seq ID No 1 and/or be encoded by the nucleotide sequence of Seq ID No 2 or a fragment thereof.

The labelled antibody may thus be a labelled, recombinant, single chain, variable fragment of monoclonal immunoglobulin (scFv) directed to mycolic acids. The blank sample may be phosphate buffered saline. The labelled antibody is accordingly specific for antigens arising from mycobacterial infection.

The method of the invention can be used in all humoral fluid tuberculosis diagnostics, such as those using serum, plasma, pleural fluid, peritoneal exudate fluid and cerebrospinal fluid. The method of the invention will preferably be carried out using a lateral flow immunoassay device. The analyte may thus be the human serum antibody to the mycolic acid antigen, and/or the mycolic acid antigen itself and the sample of human or animal origin may thus be selected from blood samples, spinal fluid samples and samples that naturally contain antibodies and, if the human or animal has active mycobacterial disease, the sample will contain antibodies to the mycobacterial pathogen.

The method may include allowing the exposed samples to be transferred to the control zone, after interaction with the capture zone so that remaining labelled monoclonal immunoglobulin or fragments thereof can bind to anti-immunoglobulin antibodies immobilized in the control zone to produce a coloured signal indicating that the lateral flow of reagents occurred and that the reagents are active.

The labelled monoclonal immunoglobulin antibody or a fragment thereof may be as hereinbefore described.

The antigen may be immobilised using the process described in Benadie et al., 2008. The presence of either mycolic acids from tuberculous mycobacteria, or antibodies directed to them in the sample serum are indicators of active tuberculosis in the human or animal from which the sample originated.

The mycolic acid antigen used for immobilization in the capture zone may be in a form selected from homogenous and heterogenous compound mixtures. The mycolic acid antigen used for immobilization in the capture zone may be immobilized on microparticles. Such methods are known to those skilled in the art. The immobilisation may be carried out according to the process of Benadie et al., 2008. The antibody component of the conjugate will preferably be directed to mycolic acid from tuberculous mycobacteria, but that does not cross-react with cholesterol. The sample may be from an HIV positive human. It may be from a child.

The invention thus provides a monoclonal antibody or fragment thereof for use in diagnosis of active tuberculosis from humoral fluid samples. The monoclonal antibody or fragment will be used, in particular, in point of care diagnostics of patient humoral fluid samples for active tuberculosis. The monoclonal antibody of the invention preferably detects mycolic acids from tubercular mycobacterial origin but does not cross-react with cholesterol. The monoclonal antibody may be a recombinant monoclonal antibody or fragment thereof and may be derived from an antibody gene library. The antibody gene library may be a germ line gene library and may be from chicken origin.

The invention further provides a method of detecting surrogate markers for active tuberculosis in a serum sample, the surrogate markers being selected from serum mycolic acid antigen arising from tuberculous mycobacterial infection, serum anti-mycolic acid antibodies arising from tuberculous mycobacterial infection or both, the method including the step of exposing a labelled monoclonal antibody having the amino acid sequence of Seq ID No 1 and/or which is encoded by the nucleotide sequence of Seq ID No 2 or a fragment thereof to the serum sample.

The invention further provides the use of a monoclonal antibody having the amino acid sequence of Seq ID No 1 and/or which is encoded by the nucleotide sequence of Seq ID No 2 or a fragment thereof in the manufacture of a device for use in a method of detecting surrogate markers for active tuberculosis in a serum sample, the surrogate markers being selected from serum mycolic acid antigen arising from tuberculous mycobacterial infection, serum anti-mycolic acid antibodies arising from tuberculous mycobacterial infection or both.

The invention further provides a monoclonal antibody having the amino acid sequence of Seq ID No 1 and/or which is encoded by the nucleotide sequence of Seq ID No 2 or a fragment thereof.

The invention further provides a method of detecting surrogate markers for active tuberculosis in a serum sample, the surrogate markers being selected from serum mycolic acid antigen arising from tuberculous mycobacterial infection, serum anti-mycolic acid antibodies arising from tuberculous mycobacterial infection or both, the method including the step of applying the serum sample and a blank sample to a lateral flow immunoassay device as claimed in any one of claims 5 to 14 inclusive.

The protein (amino acid) sequence shown in Scheme 1 (see SEQ ID No 1 and encoded by the nucleotide sequence of SEQ ID No 2) was derived from the chicken genome, except for the residues shown in bold, which were recombinantly introduced to effect expression and purification as a functional single chain variable antibody fragment (scFv)

```
                          Scheme 1

MKYLLPTAAAGLLLLAAQPAMAARWTSPGAASRRPEEGSASSARPPG
XPAVTAWVGCDRRLAKGWNGSLVLMMMVVSHTTGRRRAVPPSRGTTG
RAQGCSTTSGLRTPAPTLAPKIIILYDYRRMGPGTEVIVSSGGGGSG
GGGSGGGGSALTQPSSVSANPGEIVEITCSGSDSSNNYGWYQQKAPG
SAPVTVIYDNTNRPSNIPSRFSGSTSGSTATLTITGVQAEDEAAYFC
PSTDSIFGAGTTLTVLGQPNAAAEQKLISEEDLN

PeIB vector sequence: MKYLLPTAAAGLLLLAAQPAMA
c-Myc purification sequence: EQKLISEEDLN
Linker stabilisation sequence: GGGGSGGGGSGGGGS
```

The monoclonal scFv antibody fragment may be selected from any vertebrate immunoglobulin gene library. It may, for example, be selected from a chicken immunoglobulin gene library. Preferably, it will be selected for a particular affinity and specificity of binding to mycolic acids from experimentally mutated immunoglobulin genes or immunoglobulin gene libraries. In the method of the invention, the scFv antibody fragment can be substituted by a larger fragment of the immunoglobulin or by the full monoclonal immunoglobulin, or by a number of the fragments linked to a carrier protein.

The analyte antibodies in the sample may be of the types that demonstrate cross-reactivity towards sterols.

Figure 2:
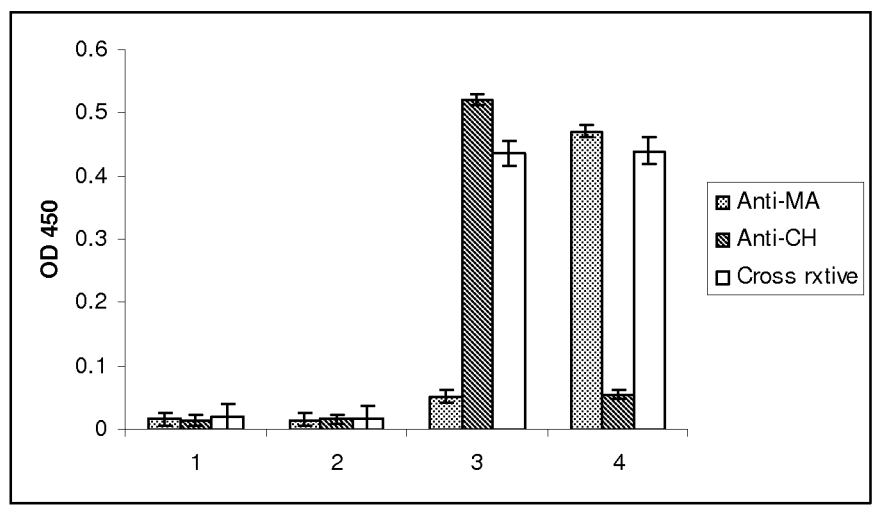

Further features of the invention will now become apparent in the following description with reference to the Figures, the following non-limiting examples and the sequence listings, in which FIG. 1 shows a typical lateral flow composition (Indicia Biotechnology), and FIG. 2 shows Chicken scFv antibody fragment recognition of mycolic acid (4=ma mix) and cholesterol (3=ch) with ELISA. Three scFv specificities were identified, which were denoted Anti-MA (grey bars), Anti-CH (black bars) and Cross rxtive (blank bars). Mycolic acid and cholesterol antigens were coated from hexane, while results on hexane only (1=Hexane) and PBS only (2=PBS) sham coated wells are indicated as well. The error bars indicate the standard deviation of four repeats.

EXAMPLE 1

Generation and Characterization of Recombinant Monoclonal scFv Antibody Fragments to Mycolic Acids and Cholesterol 1 Materials and Methods 1.1 Generation of Recombinant Monoclonal scFv 1.1.1 Phage Display Antibody Library A naive semi-synthetic chicken phage display library was used (Van Wyngaardt et al., 2004). The library contains recombinant filamentous bacteriophages displaying scFv antibody fragments. These fragments were derived from combinatorial pairings of chicken $V_H$ and $V_L$ immunoglobulin domains. $V_H$ and $V_L$ domains are linked by an interpeptide segment consisting of the sequence (GGGGS)$_3$, enabling a fold typical of single variable fragments.

1.1.2 Phage Display Antibody Selection

A selection of the phages displaying mycolic acid reactive scFv's was conducted by several panning rounds. Maxisorp immunotubes (Nunc-Immuno Tubes, Nunc, Denmark) were coated with 100 µg/ml mycolic acid (Sigma Aldrich) dissolved in distilled hexane, after which the hexane was allowed to evaporate at room temperature. Coated immunotubes were briefly washed with phosphate buffered saline (PBS, pH 7.4), then blocked with 2% skimmed milk in phosphate buffered saline (2% MPBS) for 60 min. Tubes were then exposed to $10^{12}$ transforming units of the phage library in 2% MPBS, 0.1% Tween-20 buffer for 2 hrs. Unbound phage were removed by 10× washing with PBS containing 0.1% Tween-20 followed by a further 10× wash with PBS to remove the Tween-20. Bound phage was eluted with 100 mM triethylamine and neutralized with 1M Tris, pH 7.4. For enrichment *Escherichia coli* TG1 was infected with eluted phages, grown at 30° C. in 2×TYG broth (TY broth supplemented with 2% glucose) containing 100 μg/ml ampicillin, and rescued with M13-K07 helper phage (Invitrogen). Panning was repeated four times.

1.1.3 Screening of Mycolic Acid Specific Phage Clones

Following the final panning, individual ampicillin resistant *E. coli* TG1 colonies were selected for further characterization. Colonies were grown in 2×TYG broth supplemented with 100 μg/ml ampicillin in 96-well Microtitre plates at 30° C. Phages were rescued as described previously (Van Wyngaardt et al., 2004). Phage clones were screened by enzyme-linked immunosorbent assay (ELISA) carried out with mycolic acid coated microtitre plates (Maxisorp, Nunc, Denmark). Coating was done by adding 50 μl of 100 μg/ml mycolic acid in hexane in each well and drying it overnight at room temperature. Wells were briefly washed with PBS, and blocked with 300 μl of 2% MPBS for 60 min. Phage containing supernatants (25 μl) were mixed with blocking solution (25 μl), added to each well, and incubated for 60 min at 30° C. Wells were washed three times with PBS-0.1°)/0 Tween-20. Mouse monoclonal antibody B62-FE2, specific for M13 filamentous phage, in 2% MPBS-0.1% Tween-20 (50 μl) was added to each well and further incubated for 60 min at 30° C. Bound phages were detected using rabbit anti-mouse IgG antibody conjugated with horseradish peroxidase (HRP). Signals were developed with 3,3',5,5'-tetramethylbenzidine (Pierce, USA) using the 1-stepUltra TMB ELISA substrate solution according to manufacturer's instructions. Plates were read using a Multiskan Ascent (Thermo Labsystems) plate reader at a wavelength of 450 nm.

1.1.4 DNA Sequence Determination and Analysis

Phage DNA was isolated using a NucleoSpin Plasmid kit (Macherey-Nagel, GmbH). Each scFv construct was sequenced using sequencing primers, M13 reverse and 5'-CCCTCATAGTTAGCGTAACG-3'. The sequences were determined using the Big Dye 3.1 terminator chemistry (Applied Biosystems, U.S.A) and analysed with BioEdit version 3.1.

1.1.5 Production and Purification of Mycolic Acid Reactive scFv

Selected anti-mycolic acid phage obtained from *E. coli* TG1 clones was used to infect *E. coli* HB2151 to obtain soluble scFv. Single colonies were grown to an $OD_{600}$ of 0.9 in 2× TYG broth supplemented with 100 μg/ml ampicillin at 37° C. ScFv expression was induced with isopropyl β-D-thiogalactosidase (IPTG; 1 mM) and the culture further incubated at 30° C. overnight, in glucose free media. Soluble scFv was extracted, with 1× TES buffer, from the periplasm as previously described (Hugo et al., 2002). ScFv was further affinity purified using an anti c-myc tag mAb. The column was prepared by immobilising 9E10 IgG onto aminoLink Plus gel (Pierce) according to manufacturer's instructions. Periplasmic extracts were applied and after washing with PBS, bound scFv was eluted with 100 mM triethylamine and neutralised with 1 M Tris, pH 7.4. Eluted scFv was dialyzed against 1×PBS, pH 7.4 at a MW cut-off of 10 KDa. Samples were concentrated using a Macrosep® ultrafiltration device (Pall life sciences, USA) and protein concentrations determined with a BCA protein detection kit (Pierce, USA), according to the manufacturer's instructions. Purified scFv was stored at −20° C. until further use.

1.1.6 Characterization of scFv's Binding Specificity of Mycolic Acids by Sandwich ELISA Purified scFv's were tested for their binding activity using a sandwich ELISA. Maxisorp immunoplates were coated with mycolic acid as follows: The lipid samples (250 μg) were dissolved in hexane (4 ml, distilled) and vortexed for 30 s. One vial of hexane (4 ml) served as control. Solutions were coated using a Hamilton syringe (50 μl/well) and the liquid was loaded in the centre of the wells. Lipid was visible as a circular waxy layer after 2 hours of evaporation of the hexane at room temperature. The plates were then stored in plastic bags at 4° C. overnight. Plates were blocked with 2% MPBS for 60 min at 30° C. followed by a brief washing step with PBS. ScFv samples (25 μl) were mixed with 2% MPBS (25 μl), added to the wells and incubated for 60 min. Unbound scFv was removed by 3× washing with PBS-0.1% Tween-20. Anti c-myc monoclonal antibody (AbD serotec, UK) conjugated with HPR was used to detect bound scFv fragments. Signals were developed with 3,3',5,5'-tetramethylbenzidine using the 1-stepUltra TMB ELISA substrate solution according to manufacturer's instructions. Plates were read using a Multiskan Ascent (Thermo Labsystems) plate reader at a wavelength of 450 nm.

1.2 Results and Discussion

Monoclonal scFv Antibody Fragments to Mycolic Acid and Cholesterol

Previously, high antibody binding signal with human TB negative sera against mycolic acid were observed in ELISA (Schleicher et al., 2002). It was to be due to cross-reactivity of the antibodies with cholesterol, an idea that was later confirmed (Benadie et al., 2008). The cross-reactivity could be due to a mixture of monospecific anti-cholesterol and anti-MA antibodies in the sera, or due to a true cross-reactivity where a particular antibody specificity could recognize both mycolic acid and cholesterol. It is known that all humans have anti-cholesterol antibodies in their blood circulation (Swartz et al., 1988), which may explain the high antibody activity to mycolic acids in TB negative patients. To test what mechanisms are possible for the cross-reactivity, scFv fragments expressed from a chicken antibody gene library were screened for specific binders to cholesterol and mycolic acid. Three different specificities were detected and worked up from the phage display system into monovalent, monoclonal scFv fragments. The mono-specific anti-cholesterol scFv was dubbed anti-CH, while two scFv specificities were generated against mycolic acids: one monospecific (Anti-MA) and one cross-reactive with cholesterol (Cross rxtive). FIG. 2 shows the characterization of these three scFv's with ELISA. The fact that a monoclonal and monovalent cross-reactive scFv could be found against either cholesterol or MA corroborates the conclusion reported by Benadie et al. (2008) that cholesterol and MA share antigenic structural properties. On the other hand, the finding that an scFv against mycolic acids could be found that does not cross-react with cholesterol (Anti-MA) and vice versa (Anti-CH), means that the possibility remains that anti-mycolic acid antibodies may be induced during tuberculosis that do not necessarily increase the binding activity of anti-cholesterol antibodies. This may explain why higher antibody binding activity with TB pos patient sera was found than with TB neg patient sera in two previous reports (Schleicher et al., 2002, Thanyani et al., 2008).

1.3 Conclusion

Two different scFv monoclonal antibody fragments generated from a chicken antibody gene library that recognized mycolic acids, of which one cross-reacted with cholesterol and the other not, indicated that the cross-reactivity of human patient serum between mycolic acids and cholesterol could either be due to a mixture of anti-cholesterol and anti-mycolic acids antibodies and/or due to a true cross-reactive single antibody cross-reactive specificity.

The generation of an scFv antibody fragment to mycolic acids that does not cross-react with cholesterol opens the opportunity to develop a lateral flow immunoassay for the detection of anti-mycolic acids antibodies in human patient sera as surrogate marker for active tuberculosis. A highly specific interaction would then be expected at the test line or capture zone, where the patient anti-mycolic acid antibodies and serum mycolic acids themselves will be able to prevent the binding of the conjugate scFv to the immobilized mycolic acid. In this way, a faded colour test line or capture zone will indicate that the patient has active tuberculosis, while full colour development will indicate that the scFv conjugate could bind unhindered, thereby indicating that neither anti-mycolic acids antibody nor mycolic acids abound in the sample. This would be typical of a patient with no active tuberculosis.

The invention accordingly provides a scFv monoclonal antibody fragment that recognizes mycolic acids from tuberculous mycobacteria without cross-reacting with cholesterol.

Antibodies to free mycobacterial mycolic acids in the human TB patient were not anticipated, until demonstrated for the first time in 1995 (Verschoor et al 1995, PCT/GB 95/00856, Schleicher et al. 2002). Mycolic acids were presumed to occur in nature only in covalent linkage to sugars, such as the arabinogalactan cell wall glycan of mycobacteria, or trehalose, such as in trehalose dimycolate (TDM). It was therefore not anticipated that the water insoluble mycolic acids could be secreted in an aqueous environment by mycobacteria as free fatty acid waxes, until Ohja (Ojha et al. 2008) demonstrated that free mycolic acids were secreted by *Mycobacterium tuberculosis* to create a matrix for biofilm formation into which the mycobacteria embed themselves during in vitro growth in aqueous culture medium. That antibodies to free mycolic acid antigens could act as biomarker for active tuberculosis in human TB patients infected with *Mycobacterium tuberculosis* was first shown by Verschoor (Verschoor et al, 2005) and subsequently published (Thanyani et al. 2008).

The feasibility to detect such antibodies to diagnose TB with an accuracy better than 80% was recognized in an international patent review paper in 2007 (Sekanka et al. 2007). Arguing against the feasibility of detecting antibodies to mycolic acids as biomarker for active TB was the inventors' discovery that antibodies to mycolic acids cross-react with cholesterol (Benadie et al., 2008). It was then already well-known that all humans have anti-cholesterol antibodies in their blood, which went up in concentration when the person became subject to diseases such as AIDS that follows on infection with HIV, thereby possibly interfering with the detection of antibodies to mycolic acids (Fust et al. 2005). It appeared that if monoclonal antibodies to mycolic acids could be made that were monospecific for binding to mycolic acids, i.e. that do not cross-react with cholesterol, then such antibodies could be uniquely applied in a lateral flow immunotest for tuberculosis diagnosis at the point of care. A number of lateral flow immunodiagnostic tests have been developed with monoclonal antibodies directed to protein antigens of *Mycobacterium tuberculosis*, which claim to be able to detect antibodies for the diagnosis of active TB. However, none of these has been found to meet the standards of the 1999 WHO-guidelines for feasible TB diagnostic tests, despite some having found their way into poorly regulated diagnostic markets (Dunlap et al. 2000).

The present invention is the first ever demonstration of monoclonal antibodies to mycolic acids that are not cross-reactive to cholesterol. In particular, the antibodies are clonal, recombinant antibody fragments from a synthetic chicken antibody gene library. The clonal antibody fragments can easily be reconstructed into complete monoclonal antibodies by the skilled artist for inclusion into state of the art lateral flow immunodiagnostic devices. The application in lateral flow immunodiagnostic devices of the non-cholesterol-cross-reactive monoclonal antibodies to mycolic acids of the invention provides a unique opportunity for TB diagnosis at the point of care which meet the WHO standards for a valid anti-TB diagnostic test.

REFERENCES

Al Dulayymi, J. R., Baird, M. S., Roberts, E. (2005). The synthesis of a single enantiomer of a major α-mycolic acid of *M. tuberculosis. Tetrahedron,* 61, 11939-11951.

Al Dulayymi, J. R., Baird, M. S., Roberts, E., Deysel, M., Verschoor, J. (2007). The first syntheses of single enantiomers of the major methoxymycolic acid of *Mycobacterium tuberculosis. Tetrahedron,* 63, 2571-2592.

Al Dulayymi, J. R., Baird, M. S., Roberts, E., Minnikin, D. E. (2006). The synthesis of single enantiomers of meromycolic acids from mycobacterial wax esters. *Tetrahedron,* 62, 11867-11880.

Al-Dulayymi J. R., Baird M. S., Mohammed, H., Roberts, E., Clegg, W. (2006). The synthesis of one enantiomer of the α-methyl-trans-cyclopropane unit of mycolic acids. *Tetrahedron,* 62, 4851-4862.

Beckman, E. V., Porcelli, S. A., Morita, C. T. Behar, S. M., Furlong, S. T., Brenner, M. B., 1994. Recognition of a lipid antigen by CD1-restricted αβ$^+$ T cells. Nature 372, 691-694.

Benadie, Y., Deysel, M., Siko, D. G., Roberts, V. V., Van Wyngaardt, S., Thanyani, S. T., Sekanka, G., Ten Bokum, A. M., Collett, L. A., Grooten, J., Baird, M. S., Verschoor, J. A. (2008). Cholesteroid nature of free mycolic acids from *M. tuberculosis. Chem Phys Lipids* 152, 95-103.

Brennan P. J., Nikaido H., 1995. The envelope of mycobacteria. Annu. Rev. Biochem. 64:29-63.

Butler, W. R., Jost, K. C., Kilburn, J. O., 1991. Identification of mycobacteria by high-performance liquid chromatography. J. Clin. Microbiol. 29:2468-2472.

Dobson, G., Minnikin, D. E., Minnikin, S. M., Parlett, J. H., Goodfellow, M., Ridell, M., Magnusson, M. 1985. Systematic analysis of complex mycobacterial lipids. In Chemical Methods of Bacterial Systematics (Ed. M. Goodfellow and D. E. Minnikin) 237-265. London, Academic Press.

Dunlap N E, Bass J, FujiwaraP, Hopewell P, C. Horseburgh R, Salfinger M, Simone P M. (2000) American Journal of Respiratory and Critical Care Medicine 161:1376-1395.

Fust G, Beck Z, Banhegyi D, Kocsis J, Biro A, Prohaszka Z (2005) Antibodies against heat shock proteins and cholesterol in HIV infection. Molecular Immunology 42 (2005) 79-85)

Fujiwara, N., Pan, J., Enomoto, K., Terano, Y., Honda, T., Yano, I. (1999). Production and partial characterization of anti-cord factor (trehalose-6,6P-dimycolate) IgG antibody in rabbits recognizing mycolic acid subclasses of *Mycobacterium tuberculosis* or *Mycobacterium avium*. FEMS Immunology and Medical Microbiology 24, 141-149.

Goodrum, M. A., Siko, D. G. R., Niehues, T., Eichelbauer, D., Verschoor, J. A., 2001. Mycolic acids from *Mycobacterium tuberculosis*: purification by countercurrent distribution and T-cell stimulation. Microbios 106, 55-67.

Julian, E., Matas, L., Perez, A., Alcaide, J., Laneelle, M., Luquin, M., 2002. Serodiagnosis of Tuberculosis: Comparison of Immunoglobulin A (IgA) Response to Sulfolipid I with IgG and IgM Responses to 2,3-Diacyltrehalose, 2,3,6-Triacyltrehalose, and Cord Factor Antigens. J. Clin. Microbiol. 40(10), 3782-3788.

Kivihya-Ndugga, L., van Cleeff, M., Juma, E., Kimwomi, J., Githui, W., Oskam, L., Schuitema, A., van Soolingen, D., Nganga, L., Kibuga, D., Odhiambo, J., Klatser, P., 2004. Comparison of PCR with the routine procedure for diagnosis of tuberculosis in a population with high prevalences of tuberculosis and human immunodeficiency virus. J. Clin. Microbiol. 42:1012-5.

Korf, J. E., Stoltz, A. C., Verschoor, J. A., De Baetselier, P., Grooten, J., 2005. The *Mycobacterium tuberculosis* cell wall component mycolic acid elicits pathogen-associated host innate immune responses. Eur. J. Immunol. 35:890-900.

Koza, G., Baird, M. S. (2007) The first synthesis of single enantiomers of ketomycolic acids. Tetrahedron Lett., 48, 2165-2169.

Lee, R. E., Brennan, P. J., Besra G. S., 1996, *Mycobacterium tuberculosis* cell envelope. Curr. Top. Microbiol. Immunol. 215:1-27.

Lemmer, Y., Thanyani, S. T., Vrey, P. J., Driver, C. H. S., Venter, L., van Wyngaardt, S., ten Bokum, A. M. C., Ozoemena, K. I., Pilcher, L. A., Fernig, D. G., Stoltz, A. C., Swai, H. S., Verschoor, J. A. (2009). Detection of anti-mycolic acid antibodies by liposomal biosensors. Methods Enzymol 464, 79-104.

Lopez-Marin, L. M., Segura, E., Hermida-Escobedo, C., Lemassu, A., Salinas-Carmona, M. C., 2003. 6,6'-Dimycoloyl trehalose from a rapidly growing *Mycobacterium*: an alternative antigen for tuberculosis serodiagnosis. FEMS. Immunol. Med. Microbiol. 36: 47-54.

Lyashchenko, K. P., Colangeli, R., Houde, M., Jandali, H., Menzies, D., Gennaro, M. L., 1998. Heterogeneous antibody responses in tuberculosis. Infect. Immun. 66(8), 3936-3940.

Mathebula, N. S., Pillay, J., Toschi, G., Verschoor, J. A., Ozoemena, K. I. (2009) Recognition of anti-mycolic acid antibody at self-assembled mycolic acid antigens on a gold electrode: a potential impedimetric immunosensing platform for active tuberculosis. Chem Comm 2009, 3345-3347.

Moody, D. B., Reinhold, B. B., Guy, M. R., Beckman, E. M., Frederique, D. E., Furlong, S. T., Ye, S., Reinhold, V. N., Sieling, P. A., Modlin, R. L., Besra, G. S., Porcelli, S. A., 1997. Structural requirements for glycolipid antigen recognition by CD1b-restricted T cells. Science 278, 283-286.

Moody, D. B., Reinhold, B. B., Reinhold, V. N., Besra, G. S., Porcelli S. A., 1999. Uptake and processing of glycosylated mycolates for presentation to CDb-restricted T cells. Immunol. Lett. 65, 85-91.

Nabeshima, S., Murata, M., Kashiwagi, K., Fujita, M., Furusyo, N., Hayashi, J. (2005). Serum antibody response to tuberculosis-associated glycolipid antigen after BCG vaccination in adults. J Infect Chemother 11, 256-258.

Ojha, A. K., Baughn, A. D., Sambandan, D., Hsu, T., Trivelli, X., Guerardel, Y., Alahari, A., Kremer, L., Jacobs Jr, W. R., Hatfull, G. F. (2008). Growth of *Mycobacterium tuberculosis* biofilms containing free mycolic acids and harbouring drug-tolerant bacteria. Mol Microbiol 69, 164-174).

Ozoemena, K. I., Pillay, J., Toschi, G., Verschoor, J. A. (2010). Electron transfer dynamics across self-assembled N-(2-mercaptoethyl) octadecanamide/mycolic acid layers: impedimetric insights into the structural integrity and interaction with anti-mycolic acid antibodies. Phys Chem Chem Phys, 12, 345-357.

Pan, J., Fujiwara, N., Oka, S., Maekura, R., Ogura, T., Yano, I., 1999. Anti-Cord Factor (Trehalose 6,6'-Dimycolate) IgG antibody in tuberculosis patients recognizes mycolic acid subclasses. Microbiol. Immunol. 43, 863-869.

Pottunarthy, S., Wells, V. C., Morris, A. J., 2000. A Comparison of seven tests for serological diagnosis of tuberculosis. J. Clin. Microbiol. 38, 2227-2231.

Schleicher, G. K., Feldman, C., Vermaak, Y., Verschoor, J. A., 2002. Prevalence of anti-mycolic acid antibodies in patients with pulmonary tuberculosis co-infected with HIV. Clin. Chem. Lab. Med. 40, 882-887.

Sekanka, G., Baird, M., Minnikin, D., Grooten, J. (2007). Mycolic acids for the control of tuberculosis. Expert Opin Ther Patents 17, 315-331.

Shui, G., Bendt, A. K., Pethe, K., Dick, T., Wenk, M. R. (2007). Sensitive profiling of chemically diverse bioactive lipids. J Lipid Res 48, 1976-1984.

Steingart, K. R., Henry, M., Laal, S., Hopewell, P. C., Ramsay, A., Menzies, D., Cunningham, J., Weldingh, K., Pai, M. (2007) Commercial serological antibody detection tests for the diagnosis of pulmonary tuberculosis: A Systematic Review. PLoS Medicine 4, 1041-1060.

Swartz, G. M., Gentry, M. K., Amendeo, L. M., Blanchette-Mackie, E. J., Alving, C. R. (1988). Antibodies to cholesterol. Proc. Natl. Acad. Sci. USA 85, 1902-1906.

Thanyani, S. T., Roberts, V., Siko, D. G., Vrey, P., Verschoor, J. A. (2008). A novel application of affinity biosensor technology to detect antibodies to mycolic acid in tuberculosis patients. J Immunol Methods 332, 61-72.

Toschi, G., Baird, M. S. (2006). An improved procedure for the preparation of the β-hydroxy-β-alkyl fatty acid fragment of mycolic acids. Tetrahedron 62, 3221-3227.

Verschoor, J. A., Bye, S. N., 1995. A method for detecting the presence of a *mycobacterium* species and a kit and antibodies for use therein. Patent application no. PCT/GB95/00856.

Verschoor, J. A., 1996. The isolation and purification of mycobacterial lipid cell-wall components. Patent application no. PCT/GB96/00416.

Verschoor, J. A., Lenaerts, A. & Johannsen, E., 1998. A composition comprising a carrier and a purified mycobacterial lipid cell-wall component and its use in the prevention, treatment and diagnonsis of disease. Patent application no. PCT/GB98/00681.

Verschoor, J. A., Siko, D. G. R. & Van Wyngaardt, S. (2005). A serodiagnostic method to detect antibodies to mycolic acid in tuberculosis patients as surrogate markers for infection. International patent application no. PCT/IB2005/051548 (11 May 2005).

WHO (2009). Global tuberculosis control: epidemiology, strategy, financing: WHO report. *WHO/HTM/TB* 2009, 411.

Wood, R. (2007). Challenges of TB diagnosis and treatment in South Africa. Southern *Afr J HIV Med* 27, 44-48.

Yuan, Y., Crane, D. C., Musser, J. M., Sreevatsan, S., Barry, C. E. (1997). MMAS-1, the Branch Point Between cis- and trans-Cyclopropanecontaining Oxygenated Mycolates in *Mycobacterium tuberculosis*. *J Biol Chem* 272, 10041-10049.

The invention claimed is:

1. A method for diagnosing a patient as having an active *Mycobacterium tuberculosis* infection by detecting markers selected from mycolic acid antigen arising from tuberculous mycobacterial infection, anti-mycolic acid antibodies arising from tuberculous mycobacterial infection, or both, in a serum sample from the patient, the method of detection comprising:

a) combining the serum sample with a labeled recombinant, single chain, variable fragment of monoclonal immunoglobulin (rscFv) specific for mycolic acids of mycobacterial origin, to produce a combined serum sample, wherein the labeled rscFv does not cross-react with cholesterol, and wherein the label produces a detectable signal when bound to immobilized mycolic acid antigen of mycobacterial origin;

b) combining a blank sample with the labeled rscFv to produce a combined blank sample;

c) contacting both the combined serum sample and the combined blank sample with a point of care device comprising a surface containing immobilized mycolic acid antigen of synthetic or mycobacterial origin;

d) allowing the combined serum sample and the combined blank sample to migrate along the surface so that the labeled rscFv in each sample binds to the immobilized mycolic antigen of synthetic or mycobacterial origin to produce a detectable signal; and, e) comparing the signal produced by binding of the labeled rscFvs in the combined serum sample to the immobilized mycolic antigen of synthetic or mycobacterial origin with the signal produced by binding of the labeled rscFvs in the combined blank sample to the immobilized mycolic antigen of synthetic or mycobacterial origin;

wherein if the signal obtained from binding of the labeled rscFv to the immobilized mycolic antigen of synthetic or mycobacterial origin is less than the signal produced by binding of the labeled rscFv in the combined blank sample to the immobilized mycolic antigen of synthetic or mycobacterial origin, diagnosing the patient as being infected with tuberculosis.

2. The method of claim 1, wherein the point of care device is a lateral flow immunoassay device.

3. The method of claim 1 wherein the surface further comprises immobilized anti-immunoglobulin antibodies, and wherein following binding of the labeled rscFvs to the immobilized mycolic acids, the combined serum sample is allowed to continue migrating along the membrane so that the labeled rscFvs are exposed to immobilized anti-immunoglobulin antibodies.

4. The method of claim 1, wherein the label is colloidal gold.

5. The method as claimed in claim 1, wherein the serum mycolic acid antigen is from mycobacteria selected from virulent and pathogenic tuberculous mycobacteria.

6. The method of claim 5, in which the serum mycolic acid antigen is derived from *Mycobacterium tuberculosis*.

7. The method of claim 1, in which the scFv is selected from a vertebrate immunoglobulin gene library.

8. The method of claim 7, in which the scFv is selected from a chicken immunoglobulin gene library.

9. The method of claim 1, wherein the serum anti-mycolic acid antibodies include the type that demonstrates cross-reactivity towards sterols.

10. The method of claim 1, wherein the scFv has the amino acid sequence of SEQ ID NO:1 and/or is encoded by the nucleotide sequence of SEQ ID NO:2 or a fragment thereof.

\* \* \* \* \*

SEQUENCE LISTING

```
<160> NUMBER OF SEQ ID NOS: 2

<210> SEQ ID NO 1
<211> LENGTH: 269
<212> TYPE: PRT
<213> ORGANISM: Gallus gallus
<220> FEATURE:
<221> NAME/KEY: MISC_FEATURE
<222> LOCATION: (1)..(22)
<223> OTHER INFORMATION: PelB vector sequence
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: MISC_FEATURE
<222> LOCATION: (136)..(150)
<223> OTHER INFORMATION: Linker stabilisation sequence
<220> FEATURE:
<221> NAME/KEY: MISC_FEATURE
<222> LOCATION: (258)..(269)
<223> OTHER INFORMATION: c-Myc purification sequence

<400> SEQUENCE: 1

Met Lys Tyr Leu Leu Pro Thr Ala Ala Ala Gly Leu Leu Leu Leu Ala
1               5                   10                  15

Ala Gln Pro Ala Met Ala Ala Arg Trp Thr Ser Pro Gly Ala Ala Ser
            20                  25                  30

Arg Arg Pro Glu Glu Gly Ser Ala Ser Ser Ala Arg Pro Pro Gly Xaa
        35                  40                  45

Pro Ala Val Thr Ala Trp Val Gly Cys Asp Arg Arg Leu Ala Lys Gly
    50                  55                  60

Trp Asn Gly Ser Leu Val Leu Met Met Met Val Val Ser His Thr Thr
65                  70                  75                  80

Gly Arg Arg Arg Ala Val Pro Pro Ser Arg Gly Thr Thr Gly Arg Ala
                85                  90                  95

Gln Gly Cys Ser Thr Thr Ser Gly Leu Arg Thr Pro Ala Pro Thr Leu
            100                 105                 110

Ala Pro Lys Ile Ile Ile Leu Tyr Asp Tyr Arg Arg Met Gly Pro Gly
        115                 120                 125

Thr Glu Val Ile Val Ser Ser Gly Gly Gly Ser Gly Gly Gly Gly
    130                 135                 140

Ser Gly Gly Gly Gly Ser Ala Leu Thr Gln Pro Ser Ser Val Ser Ala
145                 150                 155                 160

Asn Pro Gly Glu Ile Val Glu Ile Thr Cys Ser Gly Ser Asp Ser Ser
                165                 170                 175

Asn Asn Tyr Gly Trp Tyr Gln Gln Lys Ala Pro Gly Ser Ala Pro Val
            180                 185                 190

Thr Val Ile Tyr Asp Asn Thr Asn Arg Pro Ser Asn Ile Pro Ser Arg
        195                 200                 205

Phe Ser Gly Ser Thr Ser Gly Ser Thr Ala Thr Leu Thr Ile Thr Gly
    210                 215                 220

Val Gln Ala Glu Asp Glu Ala Ala Tyr Phe Cys Pro Ser Thr Asp Ser
225                 230                 235                 240

Ile Phe Gly Ala Gly Thr Thr Leu Thr Val Leu Gly Gln Pro Asn Ala
```

```
                    245                 250                 255
Ala Ala Glu Gln Lys Leu Ile Ser Glu Glu Asp Leu Asn
                260                 265

<210> SEQ ID NO 2
<211> LENGTH: 807
<212> TYPE: DNA
<213> ORGANISM: Gallus gallus

<400> SEQUENCE: 2
atgaaatatc ttcttcctac tgctgctgct ggtcttcttc ttcttgctgc tcaacctgct      60
atggctgctc gttggacttc tcctggtgct gcttctcgtc gtcctgaaga aggttctgct     120
tcttctgctc gtcctcctgg ttttcctgct gttactgctt gggttggttg tgatcgtcgt     180
cttgctaaag gttggaatgg ttctcttgtt cttatgatga tggttgtttc tcatactact     240
ggtcgtcgtc gtgctgttcc tccttctcgt ggtactactg gtcgtgctca aggttgttct     300
actacttctg gtcttcgtac tcctgctcct actcttgctc ctaaaattat tattctttat     360
gattatcgtc gtatgggtcc tggtactgaa gttattgttt cttctggtgg tggtggttct     420
ggtggtggtg gttctggtgg tggtggttct gctcttactc aaccttcttc tgtttctgct     480
aatcctggtg aaattgttga aattacttgt tctggttctg attcttctaa taattatggt     540
tggtatcaac aaaaagctcc tggttctgct cctgttactg ttatttatga taatactaat     600
cgtccttcta atattccttc tcgttttttct ggttctactt ctggttctac tgctactctt     660
actattactg gtgttcaagc tgaagatgaa gctgcttatt tttgtccttc tactgattct     720 attttggtg ctggtactac tcttactgtt cttggtcaac ctaatgctgc tgctgaacaa     780
aaacttattt ctgaagaaga tcttaat                                         807
```